United States Patent
Beck (10) Patent No.: US 10,402,974 B2
(45) Date of Patent: Sep. 3, 2019

(54) METHOD AND APPARATUS FOR EVALUATION OF MEDICAL DATA HAVING A TEMPORAL RESOLUTION

(71) Applicant: Siemens Healthcare GmbH, Erlangen (DE)

(72) Inventor: Thomas Beck, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 95 days.

(21) Appl. No.: 15/720,081

(22) Filed: Sep. 29, 2017

(65) Prior Publication Data

US 2018/0089830 A1  Mar. 29, 2018

(30) Foreign Application Priority Data

Sep. 29, 2016  (DE) .................. 10 2016 218 899

(51) Int. Cl.
*G06T 7/00* (2017.01)
*G06T 7/32* (2017.01)
(Continued)

(52) U.S. Cl.
CPC .......... *G06T 7/0016* (2013.01); *A61B 5/0042* (2013.01); *A61B 5/055* (2013.01);
(Continued)

(58) Field of Classification Search
CPC ......... G06T 7/0016; G06T 7/248; G06T 7/32; G06T 3/0068; G06T 2207/30004; G06T 2207/10088; G06T 2207/30168; G06T 2207/30016; A61B 5/0042; A61B 5/7203; A61B 5/055; A61B 5/0555; A61B 2576/026; G01R 33/5608; G01R 33/56509; G01R 33/4806; G01R 33/565
See application file for complete search history.

(56) References Cited

U.S. PATENT DOCUMENTS

2008/0304744 A1* 12/2008 Peters .................. G06T 9/001
                                                              382/173
2017/0307714 A1* 10/2017 Okell .................... A61B 5/026
2017/0340272 A1* 11/2017 Ereshefsky ........... G16H 50/50

OTHER PUBLICATIONS

Larkman et al; "Use of Multicoil Arrays for Separation of Signal from Multiple Slices Simultaneously Excited", Journal of Magnetic Resonance Imaging; vol. 13; pp. 313-317; (2001).
(Continued)

*Primary Examiner* — Qian Yang
(74) *Attorney, Agent, or Firm* — Schiff Hardin LLP (57) ABSTRACT

In a method and an evaluation computer for evaluating medical data having a temporal resolution, a preprocessing phase and a postprocessing phase, are executed. The medical data include a first dataset acquired at a first time point of the temporal resolution and a second dataset acquired at a second time point of the temporal resolution. The preprocessing of the first dataset is performed in a first time period and the preprocessed first dataset is provided as an output. The preprocessing of the second dataset is performed in a second time period and the preprocessed second dataset is provided as an output, and an interactive preparation of the postprocessing is carried out in the second time period based on the preprocessed first dataset. The medical data are evaluated by postprocessing using the preprocessed first dataset and/or the preprocessed second dataset.

17 Claims, 3 Drawing Sheets

(51) Int. Cl.
- *G06T 7/246* (2017.01)
- *A61B 5/055* (2006.01)
- *G01R 33/56* (2006.01)
- *G01R 33/565* (2006.01)
- *G06T 3/00* (2006.01)
- *G01R 33/48* (2006.01)
- *A61B 5/00* (2006.01)

(52) U.S. Cl.
CPC ........ *A61B 5/7203* (2013.01); *G01R 33/4806* (2013.01); *G01R 33/565* (2013.01); *G01R 33/5608* (2013.01); *G01R 33/56509* (2013.01); *G06T 3/0068* (2013.01); *G06T 7/248* (2017.01); *G06T 7/32* (2017.01); *A61B 5/0555* (2013.01); *A61B 2576/026* (2013.01); *G06T 2207/10088* (2013.01); *G06T 2207/30004* (2013.01); *G06T 2207/30016* (2013.01); *G06T 2207/30168* (2013.01)

(56) References Cited

OTHER PUBLICATIONS

Yan et al. "DPARSF: a MATLAB toolbox for "pipeline" data analysis of resting-state fMRI" Front. Syst. Neurosci. vol. 4, Article 13, (2010).

Souza et al: "SIMA: Simultaneous Multislice Acquisition of MR Images by Hadamard-Encoded Excitation", in: Journal of Computer Assisted Tomography vol. 12, No. 6, pp. 1026-1030, (1988).

Thesen et al: "Prospective Acquisition Correction for Head Motion With Image-Based Tracking for Real-Time fMRI," Magnetic Resonance in Medicine 44, pp. 457-465, (2000).

Breuer, et. al.: "Controlled Aliasing in Parallel Imaging Results in Higher Acceleration (CAIPIRINHA) for Multi-Slice Imaging", in: Magnetic Resonance in Medicine, vol. 53, No. 3, pp. 684-691; (2005).

Greicius, et al.: "Functional connectivity in the resting brain: A network analysis of the default mode hypothesis", PNAS, 7. vol. 100, No. 1, pp. 253-258, (2003).

* cited by examiner

METHOD AND APPARATUS FOR EVALUATION OF MEDICAL DATA HAVING A TEMPORAL RESOLUTION

BACKGROUND OF THE INVENTION

Field of the Invention

The present invention concerns a method, an evaluation computer, a medical imaging apparatus, and an electronically readable data storage medium encoded with programming instructions, for evaluating medical data having a temporal resolution.

Description of the Prior Art

In medical imaging, medical data are typically acquired that represent a section of an examination subject, in particular an examination region of interest, in three-dimensional form, if necessary with an additional temporal resolution. Due to improvements in medical imaging devices, it is possible to generate image data at a higher resolution, which leads to an increase in the amount of medical data. A recently developed acquisition technique, for example, is a method combined with simultaneous multi-slice for recording a BOLD contrast in functional magnetic resonance imaging (fMRI). Within the scope of the corresponding evaluation, a resting-state analysis is typically performed in order to analyze the neural resting state of the examination subject. The execution of a complex and time-intensive algorithm is typically necessary for this purpose.

The evaluation of medical data acquired in such a way requires a number of steps, many of which can be executed in an automated manner, whereas other steps require a prior parameterization by a user. Complex dependencies exist between individual steps of the evaluation and predefinable parameters, particularly for the evaluation of medical data acquired by a resting-state method for functional MR imaging.

SUMMARY OF THE INVENTION

An object of the present invention is to provide a particularly simple and time-saving method for evaluating medical data having a temporal resolution.

The inventive method for evaluating medical data having a temporal resolution includes a preprocessing phase and a postprocessing phase. The medical data include a first dataset acquired at a first time point of the temporal resolution and a second dataset acquired at a second time point of the temporal resolution. In accordance with the inventive method, the preprocessing of the first dataset is performed by a computer in a first time period so as to produce a preprocessed first dataset, the preprocessing of the second dataset is performed by the computer in a second time period so as to produce preprocessed second dataset. An interactive preparation of the postprocessing is carried out using the computer, and the evaluation of the medical data takes place by postprocessing of the preprocessed first dataset and/or the preprocessed second dataset using the interactively prepared postprocessing.

Medical data are typically acquired from an examination subject by a medical imaging device, the medical data preferably being used to produce a clinical diagnosis. Medical data may be raw data that are processed further and/or evaluated, so that an analysis of the medical data can be conducted. The medical data are reconstructed into image data for this purpose. Medical data may also be image data that represent anatomy and/or a pathology of an examination subject. Medical data and/or the medical data reconstructed into image data may be present in two-dimensional or three-dimensional form. Medical data of this type typically image the examination subject and/or a section of the same at a specific point in time, the point in time being determined by the time instant of the acquisition. The medical data may also be spatially resolved quantitative and/or qualitative values. Quantitative and/or qualitative values of this type, for example, may be information relating to a functionality of an organ within the examination region.

Typically, a number of acquisitions at a number of time points are necessary for a temporally resolved examination of an examination subject. In this case a dataset is acquired at each time point, the time interval between two time points defining the temporal resolution. The medical data then are composed of multiple datasets. In particular, the medical data include a first dataset acquired at a first time point and a second dataset acquired at a second time point. Typically, the acquisition of a dataset requires an acquisition period composed of a number of time points. The acquisition of a dataset at a time point means that the dataset is assigned to that time point, that time point being within the acquisition period of the dataset when considered with respect to time. The medical data preferably include further data that has been acquired at further time points. The time interval between the acquisition of each two datasets is preferably of equal length. The at least two datasets preferably image the same section of the examination subject, in particular the same examination region. Preferably, the only difference in the acquisition of the at least two datasets is the time point of the acquisition. When the temporally resolved medical data are four-dimensional data, then a dataset of the medical data can be reconstructed into three-dimensional image data that represent the examination region. When the temporally resolved medical data are three-dimensional data, then a dataset of the medical data can be reconstructed into two-dimensional image data that, for example, represent the examination region as a projection.

The evaluation of the medical data may be a reconstruction of the medical data into image data. The evaluation of the medical data may also be an analysis, organized such that the evaluated medical data permits an assessment of a function of an organ, for example. The evaluation is typically geared to the medical data and/or the method by which the medical data was acquired. For example, the medical data can be magnetic resonance data that have been acquired by a functional MR imaging method, the examination region being the brain of an examination subject. The evaluation may be a reconstruction of the medical data into image data, a determination of a spatially resolved oxygenation of the brain and/or a spatially resolved determination of an activity of the brain. The medical data may be a number of datasets. An evaluation typically involves a number of method steps, in which case the method steps can be classified into at least two categories. A first of the at least two categories can be the preprocessing phase and a second of the at least two categories can be the postprocessing phase.

When the medical data is composed of at least two datasets, the preprocessing is preferably carried out individually and/or separately for each of the at least two datasets. The preprocessing of a first of the at least two datasets is performed in the first time period. The preprocessing of a second of the at least two datasets is performed in the second time period. Considered with respect to time, the second time period comes after the first time period.

Preferably, the same algorithm is applied during the preprocessing of the first dataset as during the preprocessing of the second dataset. The preprocessing is typically performed automatically and/or requires no input and/or prior specification of a parameter. The preprocessing is preferably performed based on the datasets included in the medical data and an algorithm, the medical data and the algorithm being provided for the preprocessing. Typically, further datasets included in the medical data and/or the medical data are required for the complete preprocessing of a dataset. At least one substep in the preprocessing, which substep is typically carried out individually and/or separately for each of the at least two datasets, is performed based on a single dataset of the at least two datasets.

The preprocessing of the medical data is carried out on the basis of the preprocessing of the datasets included in the medical data and, where applicable, on the basis of at least one preprocessing phase relating to a number of datasets included in the medical data and/or the medical data. The preprocessing of multiple datasets included in the medical data and/or the medical data can be carried out in the first time period and/or in the second time period and/or in a time period preceding the first time period and/or in a time period succeeding the second time period and/or between the first time period and the second time period. The preprocessed medical data are preferably taken into account during the postprocessing.

During the preprocessing of the medical data and/or of a dataset, the medical data are typically normalized and/or standardized so that the resulting preprocessed medical data, in particular the preprocessed first dataset and the preprocessed second dataset, are free of external influences, which external influences have occurred during the acquisition of the medical data. An external influence of this type may for example be a change in a physical variable, such as the temperature, for example, where the mode of operation of the medical imaging device may be dependent on this physical variable. As a result, the medical data may also be dependent on this physical variable. Furthermore, the preprocessing may include a normalization and/or standardization with respect to the examination subject. The preprocessing may also include an extraction of a property of a dataset. The preprocessing is intended to eliminate changes and/or external influences during the acquisition of the medical data at at least two time points that are different from one another during the temporal resolution. A difference between the first dataset and the second dataset that is attributable to an external influence during their acquisition is preferably eliminated in the course of the preprocessing. Preprocessed medical data and/or datasets are typically free of errors and/or artifacts and/or exhibit a reduced number of errors and/or artifacts. A substep which is included in the preprocessing and is typically performed individually and/or separately for each of the at least two datasets is a slice-time correction, for example. Particularly in MR imaging and/or in computed tomography, the first dataset of the examination region can be acquired slice by slice, with individual slices being acquired at slightly different time points, a representative first time point being assigned to the acquisition of the dataset of the examination region. Differences between the slightly different time points and the first time point can be corrected by the slice-time correction.

The preprocessed first dataset is also provided within the first time period in which the first dataset is preprocessed. The providing may be included in the preprocessing. The providing may be, for example, a transfer of the preprocessed first dataset to a memory or storage facility and/or a representation, in particular a visualization, of a property included in the dataset and extracted within the scope of the preprocessing. The providing is preferably implemented such that the datasets preprocessed prior to the postprocessing, when considered with respect to time, can be accessed during the postprocessing. The providing is implemented in particular such that an interactive preparation of the postprocessing can take place based on at least one provided preprocessed dataset.

Preferably, all of the already-provided preprocessed datasets are taken into account in the interactive preparation of the postprocessing. For example, a prior specification for the postprocessing based on the first dataset and/or an extracted property of the first dataset can be made during the interactive preparation. In this process, a property and/or information relating to at least the first preprocessed dataset are/is preferably presented to a user via a user interface, so the user can influence the postprocessing on the basis thereof. For example, image data can be displayed to the user, so the user is able to select a subregion of the examination region based on the image data. Image data of this type may be based on the medical data or can be anatomical image data which are provided. The selected subregion can be taken into account during the preprocessing of the second dataset and/or during the postprocessing. The user is typically an operator of an evaluation computer that is configured for performing the inventive method.

The postprocessing is typically performed after the completion of the preprocessing, and the postprocessing is completed after the preprocessing. The method steps included in the postprocessing preferably define the type of evaluation and/or generate a result of the evaluation, on the basis of which result a physician can produce a diagnosis. Preferably, all the results required for a diagnosis are generated and/or provided by the postprocessing. During the postprocessing, complex algorithms are typically executed that proceed on the premise that the underlying preprocessed medical data are standardized and/or normalized. The postprocessing is typically performed based on the preprocessed first dataset and on the preprocessed second dataset. The postprocessing is typically performed based on the preprocessed medical data. Preferably, all the datasets included in the medical data are available in preprocessed form for the postprocessing. The postprocessing preferably starts automatically following completion of the preprocessing. Typically, further specifications and/or parameters are required for the postprocessing, which specifications and/or parameters can be entered by a user within the scope of the interactive preparation of the postprocessing, and/or for which default values can be used.

The postprocessing, however, can also start before the preprocessing is completed. The postprocessing can start while the second dataset is being processed and when the first dataset has already been preprocessed. Typically, the medical data include over one hundred datasets, such that the postprocessing can commence following completion of the preprocessing of fifty datasets, for example. The other fifty datasets can be preprocessed during and/or after the postprocessing of the first fifty preprocessed datasets. Typically, the postprocessing can be fully completed only when all of the datasets included in the medical data are available in preprocessed form.

An advantage of the inventive method is that the time required for the preprocessing can be used efficiently. Typically, more accurate results in the evaluation of medical data can be achieved when the data are available at a higher spatial and/or temporal resolution. The time required for the preprocessing typically increases with the volume, in particular with the spatial and/or temporal resolution, of the medical data. The inventive method accordingly allows a time-saving method for the evaluation of medical data, since an individual prior specification by a user and/or a specification of a parameter, which parameter is required for the postprocessing, can be made already during the preprocessing. In addition, providing a preprocessed medical dataset allows a feedback to the user while the preprocessing is still in progress. This enables the quality of the preprocessing and/or the quality of the medical data to be already assessed prior to completion of the evaluation, in particular prior to completion of the preprocessing. The interactive preparation of the postprocessing is preferably organized such that a user is guided or instructed so that the user is able to perform all the inputs necessary for the postprocessing while the preprocessing is still in progress. A user interface is typically used for this purpose, which has a display unit and/or an input unit. This makes it possible to perform the evaluation of the medical data in an intuitive and/or simple manner. The inventive method enables the preprocessing and the postprocessing to be separated, as a result of which the postprocessing method steps, which require a prior specification and/or definition of a parameter and/or of a subregion of the examination region, are independent of the preprocessing method steps, which are to performed automatically.

In embodiment of the method, the evaluation of the medical data is carried out based on the interactive preparation of the postprocessing. According to this embodiment, specifications made within the scope of the interactive preparation are preferably taken into account during the postprocessing. These specifications typically enable an evaluation of the medical data that is individually tailored to the examination subject and/or to preferences of the user.

In another embodiment of the method, the preprocessing of a dataset includes an extraction of a movement of the examination subject, and the providing is a representation of the movement. In temporally resolved examinations, movement of the examination subject can have a negative effect on the medical data. Determining the motion that took place during the acquisition of the medical data is advantageous in order to reduce and/or eliminate artifacts and/or errors in the medical data. The quality of the evaluated medical data thus can be increased.

The preprocessing can be an extraction, in particular a determination, of a movement of the examination subject. For example, a first and/or second movement can be respectively extracted during the preprocessing of the first and/or second dataset. The first and/or second movement are/is characterized as having occurred between the first and/or second time point and a reference time point. The reference time point may be the first time point or the second time point. The reference time point is preferably the time point at which the middle dataset, when considered with respect to time, of the medical data was acquired. Typically, a fixed point is used, which is within the examination region. The fixed point may be a distinctive landmark in the image data, which can be extracted. In the event of a movement of the examination subject, the fixed point experiences a movement. The fixed point defines a reference position at the reference time point.

The first and/or second movement can be determined by the fixed point being extracted as the first and/or second position at the first and/or second time point. The first and/or second position preferably represent/represents a spatial position defined by a three-dimensional vector. The first and/or second movement are/is preferably defined by the difference between the first and/or second position and the reference position. The movement may also be a velocity and/or an acceleration. The movement can be specified as a Cartesian vector. The movement may be an orientation, and optionally at least one angle of rotation. Depending on the method used, the movement may also include additional properties such as dimensional scaling, shear information, or information relating to a deformation state of the fixed point. A first movement is preferably extracted from the first dataset. A second movement is preferably extracted from the second dataset.

An advantage of this embodiment is that upon and/or following completion of a preprocessing of the dataset, information relating to a movement during the acquisition of the dataset, and consequently relating to the quality of the dataset, can be displayed. A user interactively preparing the postprocessing based on the preprocessing thus continuously receives information relating to the movement that took place during the acquisition of the datasets. Similarly, the user is able to recognize, on the basis of the displayed movement, whether the examination subject was or is at rest during the acquisition of the medical data. As a result, the user is able to make inferences about the state of mind of the examination subject during the acquisition of the medical data.

In another embodiment of the method, the movement is represented in a temporally resolved manner. Preferably, the first time point is in this case assigned at least one coordinate of the first position and/or the second time point is assigned at least one coordinate of the second position. The coordinate can be a Cartesian coordinate or a polar coordinate, for example. The representation of the movement preferably visualizes the intensity of the movement in a temporally resolved manner, where applicable taking into account at least one degree of freedom, such as a spatial direction, and/or an axis of rotation.

An advantage of this embodiment is that the user is able to identify datasets in which an atypical movement took place during the acquisition and/or in which the fixed points were situated at a different position compared to other datasets. If necessary, the user can identify such datasets so as to exclude them from the postprocessing. This enables the postprocessing and/or the evaluation to be performed more accurately and precisely. The quality of the evaluated medical data may be increased as a result.

In another embodiment of the method, the medical data include further datasets and the representation visualizes progress in the preprocessing of the further datasets. If, in addition to the first dataset and the second dataset, the medical data has further datasets that were acquired at further time points, then usually a preprocessing of the further datasets is required for the evaluation of the medical data. This means the preprocessed further datasets are typically taken into account in the postprocessing. The preprocessing of the further datasets is performed in further time periods following the first time period and the second time period, in which case an interactive preparation of the postprocessing based on the preprocessed first and the preprocessed second dataset can take place in the further time periods concurrently with the preprocessing of the further datasets.

Following and/or upon completion of the preprocessing of a dataset, the movement extracted from the dataset can be represented, the representation being temporally resolved along a time axis that includes the first time point, the second time point, and the further time points. Upon completion of the first time period, the first time point of the time axis is preferably assigned the movement extracted from the first dataset, the second time point of the time axis and the further time points of the time axis either not being filled and/or being filled with a default value. Upon completion of the second time period, the second time point of the time axis is preferably assigned the movement extracted from the second dataset, the further time points of the time axis either not being filled and/or being filled with a default value.

Accordingly, the first time point on the time axis is preferably assigned the first movement with completion of the first time period, and the second time point is assigned the second movement with completion of the second time period. An analogous procedure is followed for the further time points. By displaying the already-extracted movements as a function of the time axis, which preferably includes all further time points of the temporal resolution, it is possible to visualize the proportion of the already-preprocessed datasets relative to all datasets included in the medical data. In this embodiment, the representation of the movement provides information about movement of the examination subject during the acquisition of the medical data and about the progress of the preprocessing. This is advantageous because a user is able to estimate how long the preprocessing will still last and/or how much time remains to the user to prepare the postprocessing while the preprocessing is still in progress. Particularly, when the medical data include more than two datasets, displaying the progress of the preprocessing in such a way is especially user-friendly. In the case of highly spatially resolved medical data, the preprocessing of a dataset can occupy several seconds. If, in addition, a high temporal resolution is present, such that the medical data has one hundred or more datasets, the user can use the duration of the preprocessing particularly effectively, because the user has knowledge of the remaining duration of the preprocessing.

In another embodiment, the method provides that the preprocessing of a dataset includes at least one of the following method steps:
  reconstruction of the dataset into image data,
  motion correction,
  drift correction,
  extraction of functional magnetic resonance data from the image data,
  noise reduction and/or smoothing of the image data.

The dataset may be the first dataset, for example, and first image data are generated in a reconstruction of the first dataset. The dataset may be the second dataset, for example, and second image data are generated in a reconstruction of the second dataset. The medical data can be provided to the rest of the method, in which event the medical data may already be present in the form of image data. If the medical data are temporally resolved, then the image data are preferably temporally resolved, such that the first dataset corresponds to first image data and/or the second dataset corresponds to second image data. If the medical data are not already provided in the form of image data, then the preprocessing of a dataset includes the reconstruction of the dataset into image data. The further method steps included in the preprocessing of the dataset and/or the postprocessing can then be performed based on the image data. This is advantageous because handling image data that represent information and/or anatomy and/or a property of the examination subject in spatially resolved form is particularly simple and/or intuitive. A reference position thus can be identified particularly easily, for example, and the quality of the acquisition of the medical data can be assessed and/or a temporal change from one time point to the next time point can be identified.

The preprocessing can include a motion correction. For this purpose, the preprocessing preferably includes an extraction of the movement, the movement being determined in a temporally resolved manner. For example, a registration, in particular a rigid registration, typically with the use of a reference position, can be carried out for this purpose. Image data, relative to which the motion correction is performed, are typically referred to as reference image data. The reference image data may be the first image data or the second image data. The reference image data may be anatomical image data. The reference image data may also be calculated image data. Individual datasets, in particular the datasets reconstructed into image data, can be modified such that at least one fixed point occurring in all of the datasets is brought into alignment with the same fixed point in the reference image data. By such a modification, in particular a spatial modification, it is possible to correct for movement that occurs between a dataset and the reference image data. An advantage of the motion correction is that in the process it is also possible to eliminate or reduce a change between the first dataset and the second dataset that is attributable to a movement of the examination subject. Residual changes that still exist between the first dataset and second dataset then can be assumed to result from a physiological process, which is to be recorded on the basis of the medical data.

A drift correction preferably corrects a change in intensity of a signal in a dataset reconstructed into image data, the change in intensity being due to the functionality of the medical imaging device. For example, the strength of the signal in the medical data may increase or decrease with the temporal resolution due to a change in temperature, in particular a heating of the medical imaging device during the acquisition of the medical data. Such a change in the intensity of the signal typically corresponds to a change in the overall signal in temporally resolved image data. Such a change in the overall signal is referred to as drift. The advantage of a correction of such drift is that a change between the first dataset and the second dataset that is attributable to an external influence on the medical imaging device and/or to the medical imaging device itself, can be eliminated. Residual changes that still exist between the first dataset and second dataset can then be assumed to result from a physiological process, which is to be recorded on the basis of the medical data.

If the medical data are magnetic resonance data acquired by a functional MR imaging method, then the preprocessing of the first or of the second dataset may include an extraction of the functional magnetic resonance data from the first or second image data. Preferably, the first dataset was reconstructed into first image data or the second dataset was reconstructed into second image data for this purpose. Functional magnetic resonance data typically represents brain activity in spatially resolved form. A temporal change in an intensity of a pixel due to a brain activity in the resting state typically occurs in a frequency range between 8 MHz and 150 MHz. Accordingly, intensity changes in that frequency range should be particularly readily and/or precisely detected in functional imaging. A temporal filtering of the image data, in particular a temporal filtering of the datasets corresponding to their temporal resolution, can take place for this purpose, so that signal changes outside of the specified frequency range can be excluded from the evaluation, in particular from the postprocessing of the medical data. Signal changes outside of the specified frequency range can be caused by breathing and/or heartbeat. The extraction of functional magnetic resonance data from the image data is typically based on a number of datasets, preferably on all of the medical data, and/or is performed within the scope of the preprocessing of the medical data. Typically, the extraction of functional magnetic resonance data within the scope of the preprocessing is not assigned to a single time period and/or a single dataset.

An advantage of such an extraction of functional magnetic resonance data is that it allows an evaluation of the functional magnetic resonance data to be carried out precisely. External influences, in particular physiological and unavoidable influences, such as breathing and/or heartbeat of the examination subject, can be eliminated and/or reduced.

The preprocessing may also include a noise reduction and/or smoothing. In this case the first image data or the second image data are spatially filtered such that the noise of the image data decreases and/or the image data appear more homogeneous. This can be achieved, for example, by using a filter with a Gaussian kernel, wherein the Gaussian kernel has a width of 3-4 mm at half maximum height, for example. Noise reduction and/or smoothing may also be included in the reconstruction. The effect of the noise reduction and/or smoothing of the image data is that statistical variations in the intensity of the signal can be eliminated. This enables anatomy and/or a pathology and/or a change in a signal intensity of a pixel between at least two time points, for example between the first image data and the second image data, to be more readily identified during the postprocessing. Preprocessed medical data of this type can be postprocessed more effectively, as a result of which the evaluation of the medical data is rendered more robust.

A common feature of the described preprocessing method steps is that they require no interaction of a user and/or prior specification of a parameter. The cited preprocessing method steps are preferably performed automatically.

In an embodiment of the method, the interactive preparation of the postprocessing includes at least one of the following method steps:
    assessment of a quality of the first and/or second image data,
    aborting the preprocessing,
    definition of a seed region based on the first and/or second image data and/or based on anatomical image data.

If the preprocessing of a dataset includes a reconstruction of the dataset into image data, then the image data can be displayed to a user, for example. The user can assess a quality of the image data by determining a parameter, such as a signal-to-noise ratio and/or a movement, for example. In addition, the user can compare the determined parameter with a threshold value for that parameter. The threshold value for that parameter can also be specified in advance by the user, possibly also taking into account the medical data and/or the image data and/or the examination subject and/or the type of examination. Depending on the relation of the determined parameter to the threshold value, the user can perform and/or initiate at least one further method step. For example, if the determined parameter exceeds the threshold value, such as a movement that amounts to more than 5 mm, then the user can abort the preprocessing. If the determined parameter falls below the threshold value, then the preprocessing and/or the postprocessing can be continued without interruption.

An advantage of this embodiment is that the user is able to recognize a likely quality of the medical data that is to be evaluated, already during the preprocessing. If the quality of the first and/or second image data does not meet the user's requirements, then the user can abort the preprocessing if need be. It can thereby be recognized at an earlier time point whether a repetition of the acquisition of the medical data and/or of the evaluation of the medical data, in particular of the preprocessing of the medical data, is necessary. Furthermore, due to the possibility of an interaction, the perceived amount of time required for the preprocessing can be shortened for the user. The user, who preferably monitors the inventive method, can view and assess intermediate results of the preprocessing and, based on such intermediate results, influence further method steps included in the evaluation of the medical data.

If the medical data are magnetic resonance data acquired by a functional MR imaging method, in particular a resting-state method, a correlation analysis based on temporally resolved image data and at least one seed region is typically performed within the scope of the evaluation of the medical data, in particular during the postprocessing. The temporally resolved image data preferably includes the first image data and/or the second image data. The correlation analysis preferably determines at least one subregion of the examination region, which subregion, when considered with respect to time, is active simultaneously with a seed region. Typically, a temporally resolved and spatially resolved oxygenation of the blood, which can be determined based on the medical data, is analyzed for this purpose. A seed region can be determined within the scope of the preprocessing. For this purpose, the user is presented with the first image data and/or the second image data and/or anatomical image data on a display unit. The user can specify a seed region on the basis of the displayed image data, preferably via the input unit. The seed region is preferably specified by a selection of at least one pixel of the displayed image data. The seed region itself is at least one pixel of the displayed image data but preferably the seed region is a number of spatially related pixels of the displayed image data. The seed region is preferably a subregion of the examination region. The seed region can be selected automatically. For example, an algorithm can detect a seed point and/or a seed region based on the first image data and/or the second image data and/or anatomical image data.

In medical data of this type, the first image data and/or the second image data typically have/has a low resolution, such that the first image data and/or the second image data represent anatomy and/or a pathology only imprecisely. Anatomical image data, however, represent anatomy and/or a pathology of the examination subject in a manner that allows a viewer, in particular a physician, to be able to detect structures having a size of less than 1 mm. Anatomical image data typically have a higher resolution than the first image data and/or the second image data, which are reconstructed from medical data for functional MR imaging. If the region is defined based on anatomical image data, the anatomical image data are preferably registered relative to the first image data and/or the second image data. The seed region defined on the basis of the anatomical image data can be transferred onto the first image data and/or the second image data by a registration with the first image data and/or the second image data.

If the preprocessing includes a motion correction, then the image data on the basis of which the seed region is defined preferably correspond to image data relative to which the motion correction is performed, which typically are the reference image data. The seed region defined based on the reference image data can be transferred onto the first image data and/or the second image data on the basis of the determined movement that occurred between the acquisition of the reference image data and the acquisition of the first image data and/or the second image data.

An advantage of the definition of an interactive preparation of the postprocessing with a seed region is that a parameter required for the postprocessing, in particular the seed region for a correlation analysis, can be specified already during the preprocessing. This can take place based on the first image data and/or second image data, which are/is preferably motion-corrected. This has the advantage that a user can intuitively select a seed region in the form of a pixel or a subregion of the examination region. The defined seed region is preferably transferred onto the first image data and/or the second image data with the use of a registration. If the seed region is selected based on anatomical image data, which anatomical image data are preferably registered with the first image data and/or the second image data, then the user benefits from the better image quality of anatomical image data compared to the first image data and/or the second image data, and therefore can define the seed region more precisely, as a result of which the result of the correlation analysis can be improved.

In another embodiment of the method, the postprocessing includes a correlation analysis based on a defined seed region. When the medical data are magnetic resonance data acquired by a functional MR imaging method, in particular a resting-state method, and a seed region has been defined, for example within the scope of an interactive preparation of the postprocessing, a correlation analysis based on temporally resolved image data and a seed region is typically carried out within the scope of the postprocessing. A correlation analysis is typically conducted on a seed point basis. In the process, spatially and temporally resolved intensity changes of the signal in the first image data and the second image data are analyzed, these intensity changes being caused by a change in the oxygenation of the blood. Preferably, a correlation of the intensity changes relative to an intensity change of the seed region is determined in each case for the pixels included in the examination region. The correlation is typically a temporal correlation. The correlation analysis is preferably carried out on the basis of the first image data and the second image data, which have been motion-corrected and/or drift-corrected within the scope of the preprocessing. A spatial and/or temporal filtering for noise reduction and/or in order to extract functional magnetic resonance data preferably was carried out within the scope of the preprocessing. The accuracy of the correlation analysis, and consequently the evaluation of the medical data, thus can be improved.

An advantage of a postprocessing phase that includes a correlation analysis is that magnetic resonance data acquired by a functional MR imaging method, in particular a resting-state method, can be evaluated intuitively and quickly. The interactions necessary for the evaluation can be carried out flexibly during and/or after the preprocessing. The postprocessing starts after the preprocessing, and preferably occurs automatically following prior specification of all of the information necessary for the postprocessing. This enables a very complex evaluation involving many method steps to be easily carried out for magnetic resonance data acquired by a resting-state method. The evaluation is thus robust and has little susceptibility to error. Particularly when the seed region is defined automatically, such as by execution of an algorithm, the evaluation of the medical data can be conducted in a particularly standardized and reproducible manner. An evaluation of this type can be carried out with a high level of objectivity as a result.

In another embodiment of the method, one or both of the interactive preparation of the postprocessing and the preprocessing includes a co-registration of a first and/or second dataset reconstructed into first and/or second image data with anatomical image data, with the co-registered anatomical image data being displayed overlaid with the result of the correlation analysis.

In the co-registration, at least two sets of image data that are different from one another are brought into the best possible alignment with one another. Preferably, the anatomical image data serves as reference data. Preferably, the image data of the datasets included in the medical data are co-registered individually with the reference data. Typically, during the co-registration of the first and/or second image data with the reference data, a first and/or second transformation are/is determined, which describes a necessary translation and/or rotation of the first and/or second image data in order to bring the first and/or second image data into the best possible alignment with one another and with the reference data. A co-registration of this type may be a rigid registration. The co-registration may also be an elastic registration. Typically, the co-registration requires no interaction of a user, but can be carried out automatically by execution of an algorithm. In this case it can be performed within the scope of the preprocessing of a dataset by, for example, the first dataset being reconstructed into first image data and the first image data being co-registered with the reference data. The co-registration can also be checked and/or modified by a user. A user can select fixed points in the reference image and/or the first image data and/or the second image data for the co-registration. In this case the co-registration is included in the interactive preparation of the postprocessing.

One result of the correlation analysis may be, for example, a spatially resolved color map, which visualizes a simultaneous activity of a subregion of an examination region with the seed region. The result of the correlation analysis is preferably based on the first image data and/or the second image data. Since the first image data and/or second image data are co-registered with the anatomical image data, the result of the correlation analysis, in particular the spatially resolved color map, can be displayed overlaid with the anatomical image data. In this case, a pixel of the color map preferably represents the activity and/or the correlation with the seed region of the underlying pixel of the anatomical image data. At least a part of the color map may be transparent, such that the anatomical image data are visible through the overlying color map. The color map may also be displayed for specific subregions of the examination region only. The resolution of the color map may be different from the resolution of the anatomical image data. The overlaid display may be included in the postprocessing.

An advantage of this embodiment is that the overlaid display allows the result of the correlation analysis with the anatomy and/or a pathology in the examination region to be visualized in a particularly easily intelligible way. Thus, a subregion of the brain that is active simultaneously with the seed region can be identified particularly clearly, since the anatomical image data show the anatomy and/or a pathology within the examination region distinctly, in particular at high resolution. This allows an accurate assignment of brain activity to the corresponding anatomy. Preferably, the user can select the type or an attribute of the underlying anatomical image data, in particular its contrast. The evaluation can be conducted robustly and individually for a user as a result.

In another embodiment of the method, the medical data are magnetic resonance data generated by a functional MR imaging method. Functional MR imaging is typically applied in order to conduct an examination of a brain, whereby activity in a region of the brain can be detected in a spatially and/or temporally resolved manner. The evaluation of the magnetic resonance data acquired for this purpose is complex and typically requires a number of method steps. Correction of the motion and/or a temporal drift in the signal intensity influences the quality of the evaluation. According to the inventive method, external influences of this type can be reduced by the preprocessing. The postprocessing may be, for example, generation of a color map that represents the activity of the brain in spatially resolved form. This enables the result of the evaluation of the medical data to be visualized particularly easily.

In another embodiment of the method, the medical data are magnetic resonance data generated by a resting-state method for functional MR imaging. Magnetic resonance data are acquired by a magnetic resonance scanner. A resting-state method is typically employed to examine an activity of the brain when the examination subject is in a resting state in the scanner. Typically, four-dimensional image data are generated in this case, the corresponding medical data being acquired by special acquisition techniques, such as simultaneous multi-slice (SMS). By using a technique of this kind it is possible to reduce the length of time required for the acquisition of the medical data, such as by a factor of eight. However, an accelerated acquisition of this type produces a sharp increase in the amount of magnetic resonance data that are to be evaluated, so that the evaluation typically becomes more complex and lasts longer. The acquisition of magnetic resonance data with a resting-state method, combined with simultaneous multi-slice, typically lasts between 6 and 8 minutes. Typically, 700 to 1000 datasets are generated in the process, each of which typically represents 70 to 80 slices. A comprehensive preprocessing of the datasets thus is necessary before a postprocessing phase. In particular, a correlation analysis, can be carried out. For this reason, the inventive method for magnetic resonance data acquired by a resting-state method for functional MR imaging is particularly advantageous.

In another embodiment of the method, the evaluation of the medical data overlaps in time with the generation of the medical data. Even before completion of the acquisition of the medical data, the already-acquired datasets of the medical data can be transmitted to an evaluation computer, in which the preprocessing of the transmitted datasets is already in progress. Following acquisition of a further dataset, that dataset can be transmitted to the evaluation computer and preprocessed. The postprocessing of the preprocessed medical datasets is preferably performed following acquisition and preprocessing of all of the datasets included in the medical data. According to this embodiment, the total length of time necessary for the acquisition and the evaluation of the medical data can be reduced, preferably minimized. This enables a user of the evaluation computer to be provided with a result of the evaluation within a particularly short time after commencement of the examination of the examination subject. Preferably, the evaluation of the medical data can be completed while the examination subject is still present in the practice or clinic conducting the examination. Particularly preferably, the evaluation of the medical data can be completed while the examination subject is still situated at the medical imaging device. If the quality of the evaluated medical data does not match a user's expectations and/or if no clinical diagnosis is possible based on the evaluated medical data, then time can be saved by arranging an immediate second examination of the examination subject. The quality of the preprocessed datasets can already be evaluated also during the preprocessing, and consequently during the acquisition of further datasets, and if necessary the acquisition of the medical data can be aborted and/or the acquisition of the medical data continued with modified parameters. This ensures a continuous workflow. The probability that an examination of an examination subject must be repeated can be lowered as a result.

In another embodiment of the method, the method starts automatically after the medical data have been provided. The medical data can be provided, for example, by transmission of the medical data to an evaluation computer directly following completion of the acquisition of the medical data. The medical data can be provided, for example, by transmission of the already-acquired datasets to the evaluation computer even before completion of the acquisition of the medical data, while further datasets included in the medical data are being acquired. An advantage of this embodiment is that no interaction of the user is necessary in order to start the preprocessing, which typically lasts up to several minutes. This enables a continuous workflow to be ensured, and/or resources that are used to carry out the inventive method, such as computers, to be used particularly efficiently. The evaluation of the medical data thus takes place with significant time-savings.

The invention furthermore concerns an evaluation computer configured to evaluate medical data according to the inventive method.

To that end, the evaluation computer has a preprocessor configured to perform preprocessing of the first and/or second dataset and/or to provide the preprocessed first dataset and/or the preprocessed second dataset as described above. In addition, the evaluation computer has a postprocessor configured to perform an evaluation of the medical data using the preprocessed first dataset and/or the preprocessed second dataset, while taking into account the interactive preparation as described above. The evaluation computer is connected to a user interface and/or has a user interface via which a user can perform the interactive preparation of the postprocessing based on the preprocessed first dataset.

The invention further concerns a medical imaging apparatus having such an evaluation computer. The evaluation computer may be integrated into the medical imaging apparatus. The evaluation computer may also be installed separately from the medical imaging apparatus. The evaluation computer may be connected to the medical imaging apparatus. The inventive medical imaging apparatus is thereby configured to perform the inventive method by operation of the evaluation computer.

Embodiment variants of the inventive medical imaging apparatus and the inventive evaluation computer are analogous to the embodiments of the inventive method as described above. The evaluation computer and/or the medical imaging apparatus can have further components that are necessary and/or advantageous for performing the inventive method. Computer programs and other software with which the processors of the evaluation computer automatically control and/or perform the method workflow of the inventive method can be stored in a memory of the evaluation computer.

An inventive computer program stored on a storage medium can be loaded directly into a memory of a programmable evaluation computer, having program code for performing the inventive method when the program code is executed in the evaluation computer. As a result, the inventive method can be performed quickly and in an identically reproducible and robust manner. The evaluation computer must fulfill respective requirements, such as having a suitable random access memory, a suitable graphics card or a suitable logic unit, for example, so that the respective method steps can be performed efficiently.

Examples of electronically readable data media are a DVD, a magnetic tape or a USB stick on which electronically readable control information (code) is stored.

DESCRIPTION OF THE PREFERRED
EMBODIMENTS

Figure 1:
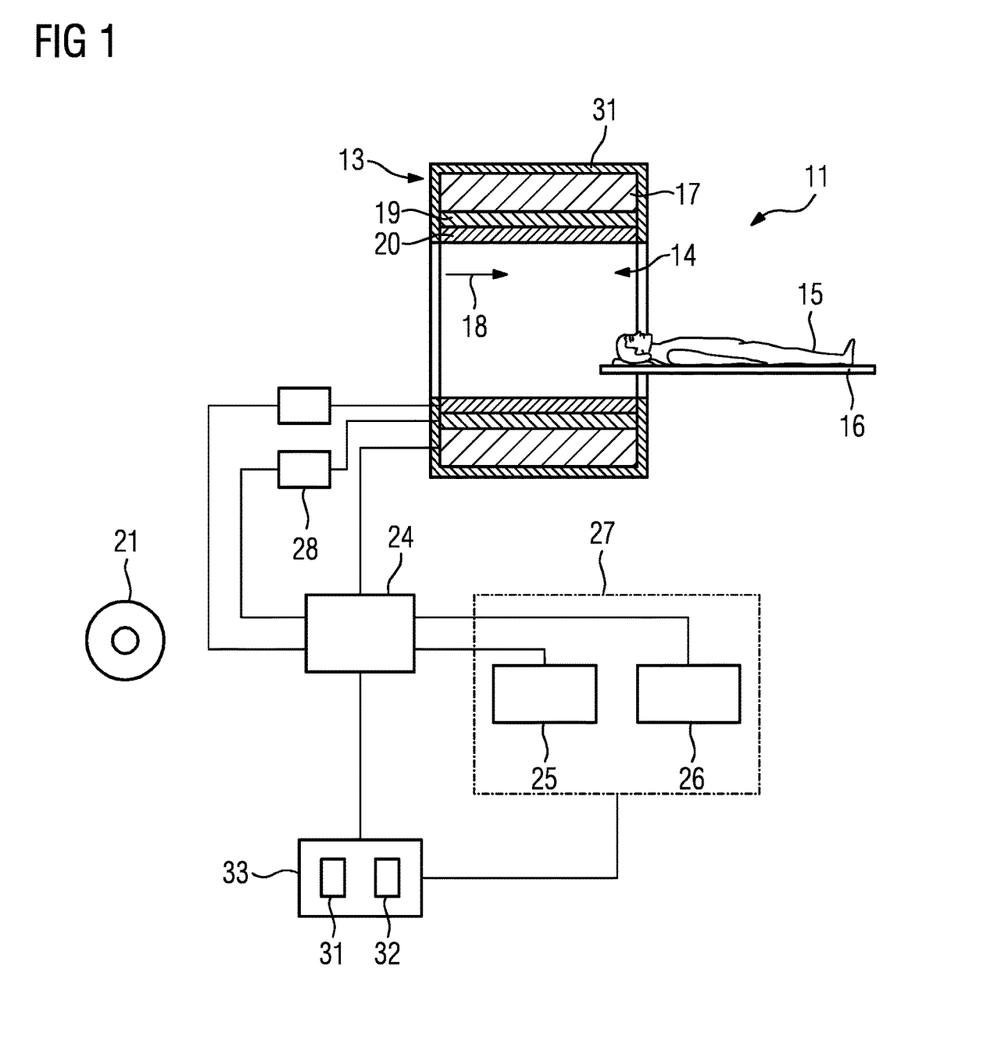
FIG. 1 is a schematic illustration of an inventive medical imaging apparatus.

FIG. 1 is a schematic illustration of a magnetic resonance apparatus 11 as an example of an inventive medical imaging device for performing the inventive method. In principle, the embodiment of the medical imaging device is not limited to the magnetic resonance apparatus 11, but can also be formed by other medical imaging devices that are deemed appropriate by those skilled in the art, such as computed tomography systems, PET systems, ultrasound devices, etc.

The magnetic resonance apparatus 11 has a scanner 13 having a basic field magnet 17 that generates a strong and constant basis magnetic field 18. The magnetic resonance scanner 11 has a cylinder-shaped patient receiving zone 14 for accommodating a patient 15, the patient receiving zone 14 being cylindrically circumferentially enclosed by the scanner 13. The patient 15 can be introduced into the patient receiving zone 14 by a patient support and positioning apparatus 16. For this purpose, the patient support and positioning apparatus 16 has a patient table that is movable inside the scanner 13.

The scanner 13 additionally has a gradient coil arrangement 19 used for spatially encoding MR signals during an imaging session. The gradient coil arrangement 19 is operated by a gradient controller 28. The scanner 13 furthermore has a radiofrequency antenna 20, which in the case shown is a bodycoil permanently integrated into the scanner 13, and a radiofrequency antenna controller 29 that operates the radiofrequency antenna 20 so as to radiate radiofrequency (RF) pulses into an examination volume that is substantially formed by the patient receiving zone 14. The radiated RF pulses excite certain nuclear spins in the patient 15 so as to give those excited spins a magnetization that deviates from the basic magnetic field 18. As those excited nuclear spins relax and return to the steady state, they emit the aforementioned MR signals, which are also RF signals, which are detected by the same antenna from which the excitation pulses were radiated, or by a different antenna.

The magnetic resonance apparatus 11 has a control computer 24 that controls the basic field magnet 17, the gradient controller 28 and the radiofrequency antenna controller 29. The control computer 24 is responsible for the centralized control of the magnetic resonance apparatus 11, such as for performing MR control sequences. In addition, the control computer 24 comprises a reconstruction processor (not shown) that reconstructs medical image data from the raw data acquired during the magnetic resonance examination. The magnetic resonance apparatus 11 has a display unit 25. Control information such as control parameters, as well as reconstructed image data, can be displayed for a user on the display unit 25, for example on at least one monitor. The magnetic resonance apparatus 11 additionally has an input unit 26 via which information and/or control parameters can be entered by a user during a measurement procedure. The control computer 24 can include the gradient controller 28 and/or the radiofrequency antenna controller 29 and/or the display unit 25 and/or the input unit 26. The display unit 25 and/or the input unit 26 can be included in a user interface 27.

The control computer 24 is connected to an evaluation computer 33. The evaluation computer 33 can be integrated into the magnetic resonance apparatus 11. The evaluation computer 33 can also be installed separately from the magnetic resonance apparatus 11. The evaluation computer 33 can be connected to the magnetic resonance apparatus 11. The evaluation computer 33 has a processor (not separately shown) for evaluating medical data having a temporal resolution. To that end, the evaluation computer 33 additionally has a preprocessor 31 and a postprocessor 32. The evaluation computer 33 is preferably connected to the user interface 27, via which an interactive preparation of the postprocessing is enabled. The evaluation computer 33 can include the user interface 27. The evaluation computer 33 is configured to carry out the method for evaluating medical data having a temporal resolution. For this purpose, the evaluation computer 33 has computer programs and/or software loaded directly into the evaluation computer 33, that have program code for carrying out the method for evaluating medical data having a temporal resolution as described herein, when the computer code is executed in the evaluation computer 33. The evaluation computer 33 is accordingly configured to carry out the inventive method. The program code can be stored on an electronically readable data medium 21 embodied separately from the evaluation computer 33, which can be loaded into the evaluation computer 33. Such code can alternatively be provided to the evaluation computer 33 over a data network.

The illustrated magnetic resonance apparatus 11 can of course have further components that are ordinarily present in magnetic resonance apparatuses. The general principle of operation of a magnetic resonance apparatus is known to those skilled in the art, so a detailed description is not necessary herein. The magnetic resonance apparatus 11 is thus configured together with the evaluation computer 33 for performing an inventive method.

An electronically readable data medium 21 is provided, on which the aforementioned electronically readable control information are stored.

Figure 2:
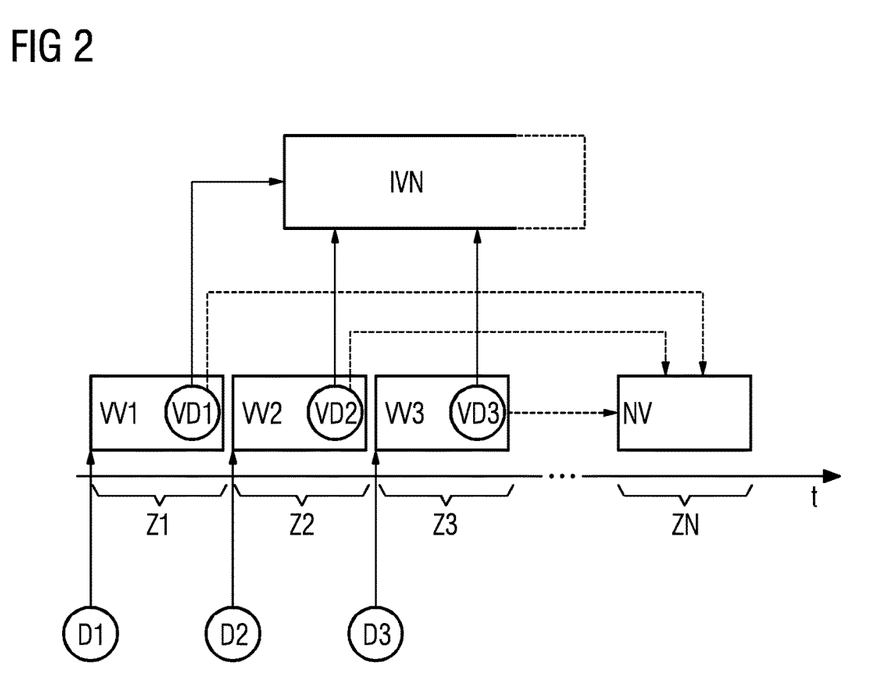
FIG. 2 is an exemplary embodiment of a workflow for an evaluation of medical data having a temporal resolution.

FIG. 2 shows an exemplary embodiment of workflow for an evaluation of medical data having a temporal resolution, comprising a preprocessing phase VV1, VV2, VV3 and a postprocessing phase NV. The medical data comprises a first dataset D1, which is assigned to a first time point of the temporal resolution, a second dataset D2, which is assigned to a second time point of the temporal resolution, and a third dataset D3, which is assigned to a third time point of the temporal resolution. The workflow of the evaluation is plotted along a horizontal timeline with time t, where the timeline does not indicate the temporal resolution of the medical data. The preprocessing VV1 of the first dataset D1 is performed in a first time period Z1, the preprocessed first dataset VD1 preferably being provided at the end of the first time period Z1. The preprocessing VV2 of the second dataset D2 is performed in a second time period Z2 following the first time period Z1, the preprocessed second dataset VD2 preferably being provided at the end of the second time period Z2. An interactive preparation of the postprocessing IVN can be performed concurrently in the second time period Z2, based for example on the preprocessed first dataset VD1. The interactive preparation of the postprocessing IVN may also begin already in the first time period Z1 and/or be performed and/or completed in full, the interactive preparation of the postprocessing IVN being performed based on provided anatomical image data, for example.

The preprocessing VV3 of the third dataset D3 is performed in a third time period Z3 following the second time period Z2, the preprocessed third dataset VD3 preferably being provided at the end of the third time period Z3. An interactive preparation of the postprocessing IVN can be performed concurrently in the third time period Z3 based on the preprocessed first dataset VD1 and/or based on the preprocessed second dataset VD2. Typically, the steps performed in the first time period Z1 and/or in the second time period Z2 are repeated and performed in sequence for all further datasets included in the medical data. In the process, an interactive preparation of the postprocessing IVN can be carried out during the preprocessing of all of the further datasets included in the medical data based on the already preprocessed and provided datasets VD1, VD2, VD3 and/or preprocessed and provided further datasets. The preprocessing VV1, VV2, VV3 is illustrated here for three datasets D1, D2, D3 by way of example. Typically, the medical data have one hundred or more datasets, dependent on the temporal resolution. A preprocessing is typically performed in a corresponding time period for each dataset included in the medical data. A preprocessing relating to the medical data as a whole can be performed in addition to the preprocessing of individual datasets. The preprocessing relating to the medical data as a whole can extend over a number of time periods Z1, Z2, Z3 and/or begin before the first time period Z1 and/or be completed within a time period Z1, Z2, Z3. The preprocessing relating to the medical data as a whole is preferably completed prior to the start of the further time period ZN.

In the embodiment illustrated in FIG. 2, a dataset D1, D2, D3 can also relate to a block of datasets. For example, the illustrated first dataset D1 can stand as representative of a first block of one hundred datasets included in the medical data. The preprocessing of this first block of one hundred datasets is performed within the scope of the preprocessing VV1 in the time period Z1, the preprocessing VV1 of the first block being completed at the end of the time period Z1 and the preprocessed first block VD1 being provided. Analogously, the second dataset D2 and/or the third dataset D3 can stand as representative of a second block and/or a third block of one hundred datasets.

Following completion of the preprocessing, the postprocessing NV is preferably performed in a further time period ZN using the preprocessed first dataset VD1 and/or the preprocessed second dataset VD2 and/or the preprocessed third dataset VD3 and/or taking into account the interactive preparation of the postprocessing IVN. The postprocessing NV may also begin prior to completion of the preprocessing VV2, VV3 if a preprocessed dataset VD1 has already been provided at the start of the postprocessing NV. If an interactive preparation of the postprocessing IVN is necessary, this can be carried out, for example, based on the preprocessed first dataset VD1. The interactive preparation of the postprocessing IVN will preferably already have been completed at the start of the postprocessing NV. The postprocessing NV can be performed concurrently with the preprocessing of further datasets VV2, VV3, such that the further time period ZN at least partially overlaps in time with the second time period Z2 and/or the third time period Z3. With the provision of further preprocessed datasets VD2, VD3, the postprocessing NV can take into account the further preprocessed datasets VD2, VD3 in addition to the preprocessed first dataset VD1.

The preprocessing VV1, VV2, VV3 of a dataset D1, D2, D3 can include at least one of the following method steps:
reconstruction of the dataset D1, D2, D3 into image data B1, B2, B3,
motion correction,
drift correction,
extraction of functional magnetic resonance data from the image data B1, B2, B3,
noise reduction and/or smoothing of the image data B1, B2, B3.

The interactive preparation of the postprocessing IVN preferably comprises at least one of the following method steps:
assessment of a quality of the first and/or second image data B1, B2,
aborting the preprocessing VV1, VV2, VV3,
definition of a seed region based on the first and/or second image data B1, B2 and/or based on anatomical image data.

In particular if the interactive preparation of the postprocessing IVN includes a definition of a seed region and/or a seed region is determined automatically during the preprocessing VV1, VV2, VV3 and/or a seed region is provided, the postprocessing NV can comprise a correlation analysis based on the defined seed region. If the interactive preparation of the postprocessing IVN and/or the preprocessing VV1, VV2, VV3 comprises a co-registration of a first and/or second and/or third dataset D1, D2, D3 reconstructed into first and/or second and/or third image data B1, B2, B3 with anatomical image data, then the co-registered anatomical image data can be displayed, for example within the scope of the postprocessing, overlaid with a result of the correlation analysis.

The evaluation of the medical data described in the workflow may overlap in time with the generation of the medical data. In particular, the medical data may comprise the first dataset D1 and optionally the second dataset D2 at the start of the first time period Z1, for example, with the third dataset D3 still being generated at this time point. The third dataset D3 has preferably already been generated in full at the start of the third time period Z3 and is included in the medical data. Typically, the medical data is provided in particular when the evaluation of the medical data does not overlap in time with the generation of the medical data. The medical data may be provided as image data B1, B2, B3. The described workflow for an evaluation of medical data having a temporal resolution then preferably starts automatically and without further interaction of a user.

Figure 3:
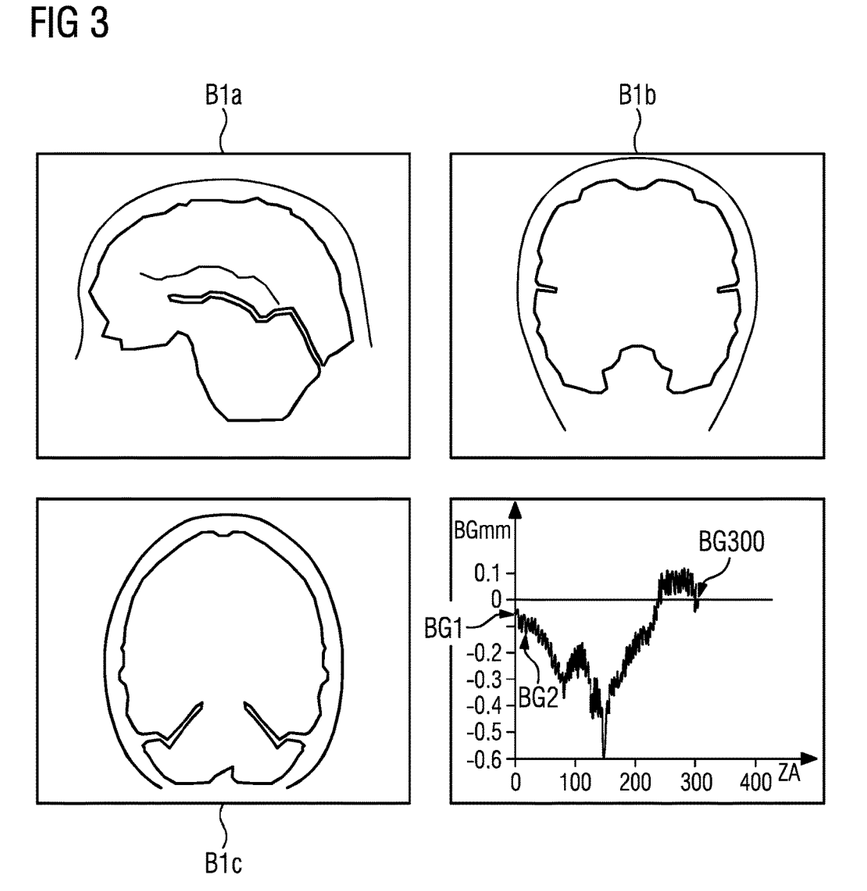
FIG. 3 shows an exemplary embodiment of a display of a result of the preprocessing for the interactive preparation of the postprocessing during the preprocessing.

FIG. 3 shows an exemplary embodiment of a display of a result of the preprocessing for the interactive preparation of the postprocessing IVN during the preprocessing. In this case the display illustrated in FIG. 3 is presented for example on a display unit 25 integrated in the evaluation unit 33 and/or associated with the evaluation unit 33. This display is typically presented during the preprocessing.

The preprocessing of a dataset may comprise an extraction of a movement. A first movement BG1 may be extracted from the first dataset D1, for example. A second movement BG2 may be extracted from the second dataset D2, for example. Each dataset may then preferably be assigned a movement BG1, BG2 in at least one, preferably in two, particularly preferably in three different spatial directions. A movement BG1, BG2 typically results from a change in a spatial position in the first and/or second image data B1, B2 compared to a reference image. The reference image may also correspond to the first image data B1 or the second image data B2. The first movement BG1 extracted from the first dataset D1 can be assigned to the first time point. The second movement BG2 extracted from the second dataset D2 can be assigned to the second time point. The movement BG1, BG2 can be provided. The providing of the movement BG1, BG2 can be a visualization of the movement BG1, BG2.

The movement BG1, BG2, BG300 illustrated in FIG. 3 comprises the movement of 300 datasets D1, D2, . . . D300, which were acquired with the temporal resolution ZA in the order in which the movement BG1, BG2, . . . BG300 of the 300 datasets D1, D2, . . . D300 is represented. The temporal resolution ZA may comprise the time points of the temporal resolution ZA and/or consecutive numbers of the datasets D1, D2, . . . D300. In the example shown, the medical data comprises 400 datasets D1, D2, . . . D400, which are preprocessed as a whole within the scope of the preprocessing. During the preprocessing, the temporal resolution ZA of all the datasets included in the medical data can be displayed, in this case a timeline with 400 consecutive numbers for the datasets D1, D2, . . . D400.

The movement BG1, BG2, . . . BG400 that occurred during the acquisition of a dataset D1, D2, . . . D400 can be displayed instantaneously after or with completion of the preprocessing VV1, VV2, . . . VV400 of said dataset D1, D2, . . . D400. Accordingly, a movement BG1, BG2, . . . BG400 can be assigned to the timeline and displayed with consecutive preprocessing VV1, VV2, . . . VV400 for each individual time point. Preferably, the preprocessing VV1, VV2, . . . VV400 of the datasets D1, D2, . . . D400 and the representation of the movement BG1, BG2, . . . BG400 take place chronologically and in ascending order of the datasets D1, D2, . . . D400, and consequently of the time points. No movement or a movement equal to zero can be displayed for time points to which no movement BG301, BG302, . . . BG400 has yet been assigned during the preprocessing. A representation of this type of the movement BG1, BG2, . . . BG400 additionally visualizes a progress of the preprocessing VV1, VV2, . . . VV400 of all of the datasets D1, D2, . . . D400.

The display of a result of the preprocessing VV1, VV2, . . . VV400 furthermore comprises a visualization B1a, B1b, B1c of image data B1. The image data B1 has for example been reconstructed from the first dataset D1 within the scope of the preprocessing VV1. Alternatively, the image data B1 may also be included in the first dataset and have been provided prior to the start of the inventive method. The image data B1 is preferably three-dimensional and in this example represents a head. In this example the image data B1 is visualized in three different orientations, producing a two-dimensional image B1a in the sagittal direction, a two-dimensional image B1b in the coronal direction and a two-dimensional image B1c in the transverse direction. A user can now assess the image data B1, for example within the scope of the interactive preparation of the postprocessing IVN, by changing the view in at least one orientation and/or assessing the quality of the image data B1 and if necessary initiating an abortion of the preprocessing VV2, VV3, . . . VV400. In the example shown, the medical data is magnetic resonance data and was generated by means of a functional MR imaging method, in particular by means of a resting-state method for functional MR imaging. The magnetic resonance data can also be generated within the scope of the inventive method.

Although modifications and changes may be suggested by those skilled in the art, it is the intention of the Applicant to embody within the patent warranted hereon all changes and modifications as reasonably and properly come within the scope of the Applicant's contribution to the art.

The invention claimed is:

1. A method for evaluating medical data having a temporal resolution, said method comprising a preprocessing phase and a postprocessing phase, said method comprising:
   in said preprocessing phase, providing medical data to a computer, said medical data comprising a first dataset acquired from a subject at a first time point of the temporal resolution and a second dataset acquired from the subject at a second time point of the temporal resolution;
   preprocessing the first dataset in said computer in a first time period, and providing the preprocessed first dataset as an output;
   preprocessing the second dataset in said computer in a second time period, and providing preprocessed second dataset as another output;
   in said computer, implementing an interactive preparation of postprocessing to be conducted in said postprocessing phase concurrently with at least one of (i) the preprocessing of the second dataset, and (ii) the acquisition of the medical data; and
   evaluating the medical data in said postprocessing phase by applying the interactively prepared postprocessing to at least one of the preprocessed first dataset or the preprocessed second dataset.

2. The method as claimed in claim 1, comprising preprocessing at least one of said first or second datasets by extracting a movement of the subject therefrom, and providing a representation of the movement in said output or said another output.

3. The method as claimed in claim 2, comprising representing the movement in said output or said another output in a temporally resolved manner.

4. The method as claimed in claim 3, wherein the medical data comprises further datasets, and comprising representing a visualized progression of the movement in preprocessing of the further datasets.

5. The method as claimed in claim 1, wherein the preprocessing of at least one of said first or second datasets comprises at least one of reconstructing the dataset into image data, motion correction, drift correction, extraction of functional magnetic resonance data from the image data, and noise reduction and/or smoothing of the image data.

6. The method as claimed in claim 1, wherein the interactive preparation of the postprocessing comprises at least one of assessment of a quality of the first and/or second image data, aborting the preprocessing, and definition of a seed region based on the first and/or second image data and/or based on anatomical image data.

7. The method as claimed in claim 1, wherein the postprocessing comprises a correlation analysis based on a defined seed region.

8. The method as claimed in claim 1, wherein at least one of the interactive preparation of the postprocessing or the preprocessing comprises a co-registration of at least one of the first or second datasets, reconstructed into first or second image data, with anatomical image data, and displaying the co-registered anatomical image data overlaid with a result of the correlation analysis.

9. The method as claimed in claim 1, wherein the medical data are magnetic resonance data acquired by a functional MR imaging method.

10. The method as claimed in claim 1, wherein the medical data are magnetic resonance data acquired by a resting-state method for functional MR imaging.

11. The method as claimed in claim 1, comprising evaluating the medical data overlapped in time with the acquisition of the medical data.

12. The method as claimed in claim 1, comprising starting the preprocessing automatically after the medical data have been provided to the computer.

13. The method as claimed in claim 1, wherein the interactive preparation of the postprocessing conducted in said postprocessing phase occurs during preprocessing of the first dataset in the first time period.

14. The method as claimed in claim 1, wherein the interactive preparation of the postprocessing conducted in said postprocessing phase is completed during preprocessing of the first dataset in the first time period.

15. An evaluation computer for evaluating medical data having a temporal resolution, said computer comprising:
a processor configured, in a preprocessing phase, to receive medical data, said medical data comprising a first dataset acquired from a subject at a first time point of the temporal resolution and a second dataset acquired from the subject at a second time point of the temporal resolution;
said processor being configured to preprocess the first dataset in a first time period, and to provide the preprocessed first dataset as an output;
said processor being configured to preprocess the second dataset in a second time period, and to provide the preprocessed second dataset as another output;
a computer configured to implement an interactive preparation of postprocessing to be conducted in a postprocessing phase concurrently with at least one of (i) the preprocessing of the second dataset, and (ii) the acquisition of the medical data; and
said computer being configured to evaluate the medical data in said postprocessing phase by applying the interactively prepared postprocessing to at least one of the preprocessed first dataset or the preprocessed second dataset.

16. A medical imaging apparatus comprising:
a control computer that acquires medical data from a subject, said medical data having a temporal resolution;
an evaluation computer configured to evaluate said medical data in a preprocessing phase and a postprocessing phase;
said evaluation computer, in said preprocessing phase, being configured to receive medical data, said medical data comprising a first dataset acquired from a subject at a first time point of the temporal resolution and a second dataset acquired from the subject at a second time point of the temporal resolution;
said evaluation computer being configured to preprocess the first dataset in said computer in a first time period, and to provide preprocessed first dataset as an output;
said evaluation computer being configured to preprocess the second dataset in said computer in a second time period, and to provide preprocessed second dataset as another output;
said evaluation computer being configured to implement an interactive preparation of postprocessing to be conducted in said postprocessing phase concurrently with at least one of (i) the preprocessing of the second dataset, and (ii) the acquisition of the medical data; and
said evaluation computer being configured to evaluate the medical data in said postprocessing phase by applying the interactively prepared postprocessing to at least one of the preprocessed first dataset or the preprocessed second dataset.

17. A non-transitory, computer-readable data storage medium encoded with programming instructions, said storage medium being loaded into a computer of a medical data acquisition apparatus from which medical data, having a temporal resolution, are acquired, said programming instructions causing said computer to:
evaluate said medical data in a preprocessing phase and a postprocessing phase;
in said preprocessing phase, receive medical data comprising a first dataset acquired from a subject at a first time point of the temporal resolution and a second dataset acquired from the subject at a second time point of the temporal resolution;
preprocess the first dataset in said computer in a first time period, and provide preprocessed first dataset as an output;
preprocess of the second dataset in said computer in a second time period, and provide preprocessed second dataset as another output;
implement an interactive preparation of postprocessing to be conducted in said postprocessing phase concurrently with at least one of (i) the preprocessing of the second dataset, and (ii) the acquisition of the medical data; and
evaluate the medical data in said postprocessing phase by applying the interactively prepared postprocessing to at least one of the preprocessed first dataset or the preprocessed second dataset.

* * * * *